(12) United States Patent
Pawloski et al.

(10) Patent No.: US 7,315,033 B1
(45) Date of Patent: Jan. 1, 2008

(54) METHOD AND APPARATUS FOR REDUCING BIOLOGICAL CONTAMINATION IN AN IMMERSION LITHOGRAPHY SYSTEM

(75) Inventors: Adam R. Pawloski, San Jose, CA (US); Harry J. Levinson, Saratoga, CA (US); Jongwook Kye, Pleasanton, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 316 days.

(21) Appl. No.: 11/121,437

(22) Filed: May 4, 2005

(51) Int. Cl.
*A61N 5/00* (2006.01)

(52) U.S. Cl. .............. 250/492.2; 355/30; 355/55; 355/71; 355/77; 396/604; 396/611; 356/239.2; 356/401; 430/311; 430/322; 430/323

(58) Field of Classification Search .......... 250/492.2; 355/30, 53, 55, 71, 77; 396/604, 611; 356/239.2, 356/401; 359/507, 811; 430/311, 322, 323
See application file for complete search history.

(56) References Cited

U.S. PATENT DOCUMENTS

| | | | |
|---|---|---|---|
| 6,466,365 B1 * | 10/2002 | Maier et al. | 359/355 |
| 6,496,257 B1 * | 12/2002 | Taniguchi et al. | 356/239.2 |
| 7,145,641 B2 * | 12/2006 | Kroon et al. | 355/71 |
| 2004/0125351 A1 | 7/2004 | Krautschik | |
| 2004/0207824 A1 | 10/2004 | Lof et al. | |
| 2004/0257544 A1 | 12/2004 | Vogel et al. | |
| 2005/0007570 A1 | 1/2005 | Streefkerk et al. | |
| 2005/0018155 A1 | 1/2005 | Cox et al. | |
| 2005/0024609 A1 | 2/2005 | De Smit et al. | |
| 2005/0078286 A1 * | 4/2005 | Dierichs et al. | 355/30 |
| 2006/0132731 A1 * | 6/2006 | Jansen et al. | 355/30 |

OTHER PUBLICATIONS

Morris, Christopher G., editor. Academic Press Dictionary of Science and Technology [online]. San Diego: Academic Press, 1992 [retrieved on May 8, 2007]. Retrieved from the Internet: <URL:http://www.xreferplus.com/entry.jsp?xrefid=3150636&secid=.-&hh=1>"reflective coating".*

* cited by examiner

*Primary Examiner*—Jack Berman
*Assistant Examiner*—Meenakshi S Sahu
(74) *Attorney, Agent, or Firm*—Renner, Otto, Boisselle & Sklar, LLP (57) ABSTRACT

Disclosed are a method of reducing biological contamination in an immersion lithography system and an immersion lithography system configured to reduce biological contamination. A reflecting element and/or an irradiating element is used to direct radiation to kill biological contaminates present with respect to at least one of i) a volume adjacent a final element of the projection system or ii) an immersion medium supply device disposed adjacent the final element.

20 Claims, 3 Drawing Sheets

METHOD AND APPARATUS FOR REDUCING BIOLOGICAL CONTAMINATION IN AN IMMERSION LITHOGRAPHY SYSTEM

TECHNICAL FIELD

The present invention relates generally to the field of lithography, which can be used, for example, in the production of integrated circuits. More particularly, the present invention relates to a method and apparatus for reducing biological contamination in an immersion lithography system.

BACKGROUND

The formation of various integrated circuit (IC) structures on a wafer often relies on lithographic processes, sometimes referred to as lithography or photolithography. For instance, patterns can be formed from a photo resist (PR) layer by passing light energy through a mask (or reticle) having an arrangement to image the desired pattern onto the PR layer. As a result, the pattern is transferred to the PR layer. In areas where the PR is sufficiently exposed and after a development cycle, the PR material can become soluble such that it can be removed to selectively expose an underlying layer (e.g., a semiconductor layer, a metal or metal containing layer, a dielectric layer, etc.). Portions of the PR layer not exposed to a threshold amount of light energy will not be removed and serve to protect the underlying layer. The exposed portions of the underlying layer can then be etched (e.g., by using a chemical wet etch or a dry reactive ion etch (RIE)) such that the pattern formed from the PR layer is transferred to the underlying layer. Alternatively, the PR layer can be used to block dopant implantation into the protected portions of the underlying layer or to retard reaction of the protected portions of the underlying layer. Thereafter, the remaining portions of the PR layer can be stripped.

There is a pervasive trend in the art of IC fabrication to increase the density with which various structures are arranged. As a result, there is a corresponding need to increase the resolution capability of lithography systems. One promising alternative to conventional optical lithography is a next-generation lithographic technique known as immersion lithography. In immersion lithography, a liquid immersion medium is placed between the final optical element of a lithography system and the wafer to be imaged. The patterned light is transmitted to the wafer through the immersion medium. The immersion medium replaces a gaseous or vacuum chamber gap that is conventionally present between the final lens of a dry lithography imaging system and the wafer. Immersion lithography has been found to enhance imaging of the wafer by increasing the refractive index of the material disposed between the final element of the projection system and the wafer. Also, the effective numerical aperture of the system can be increased, which can lead to an increase in depth of focus.

However, attempts to implement immersion lithography have encountered a number of challenges. For example, contaminants in the immersion medium and/or on parts that control the flow of the immersion medium can adversely affect the quality of the exposure pattern incident on the wafer. One particular problem has been the growth of biological contaminants (e.g., bacteria, algae, etc.) on and in parts that come in contact with the immersion medium. In the past, attempts have been made to control the presence of biological contaminants by using hydrogen peroxide or by using an ozone cleaning method. However, these techniques involve the introduction of chemicals into at least a part of the lithography system, which can lead to increased wear of system components and/or can lead to the introduction of defects when imaging a wafer.

Accordingly, there exists a need in the art for improved immersion lithography systems and associated methods of controlling biological contamination in the immersion lithography systems.

SUMMARY OF THE INVENTION

According to one aspect of the invention, a method of reducing biological contamination in an immersion lithography system includes placing a reflecting element with respect to an optical axis of a projection system of the lithographic system; and exposing the reflecting element with an exposure dose, the reflecting element redirecting radiation from the exposure dose to kill biological contaminates present with respect to at least one of i) a volume between a final element of the projection system and the reflecting element or ii) an immersion medium supply device disposed adjacent the volume.

According to another aspect of the invention, method of reducing biological contamination in an immersion lithography system includes placing an irradiating element with respect to an optical axis of a projection system of the lithographic system; and directing radiation from the irradiating element to kill biological contaminates present with respect to at least one of i) a volume adjacent a final element of the projection system or ii) an immersion medium supply device disposed adjacent the final element.

According to yet another aspect of the invention, an immersion lithography system configured to reduce biological contamination includes a projection system having a final element; an immersion medium supply device adjacent the final element; and a reflecting element placed with respect to an optical axis of the projection system such that a volume is formed between the final element and the reflecting element, and when the reflecting element is exposed with an exposure dose the reflecting element redirects radiation from the exposure dose to kill biological contaminants present with respect to at least one of the volume or the immersion medium supply device.

According to still another aspect of the invention, an immersion lithography system configured to reduce biological contamination includes a projection system having a final element; an immersion medium supply device adjacent the final element; and an irradiating element placed with respect to an optical axis of the projection system to direct radiation to kill biological contaminants present with respect to at least one of a volume adjacent the final element or the immersion medium supply device.

BRIEF DESCRIPTION OF DRAWINGS

These and further features of the present invention will be apparent with reference to the following description and drawings, wherein.

DISCLOSURE OF INVENTION

In the description that follows, like components have been given the same reference numerals, regardless of whether they are shown in different embodiments. To illustrate an embodiment(s) of the present invention in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

The description herein is presented in the exemplary context of equipment used for the fabrication of a wafer having an integrated circuit (IC) formed thereon. Example integrated circuits include general purpose microprocessors made from thousands or millions of transistors, a flash memory array or any other dedicated circuitry. However, one skilled in the art will appreciate that the methods and devices described herein can also be applied to the fabrication of any article manufactured using lithography, such as micromachines, disk drive heads, gene chips, micro electromechanical systems (MEMS) and so forth.

The apparatus and methods described herein can provide for reducing the presence and/or growth of biological contaminants in an immersion lithography system. Electromagnetic radiation normally used to image a wafer is used to kill biological contaminants (e.g., bacteria, algae, mold, etc.) that may become present on surfaces of components of the immersion lithography system and/or in the immersion medium. For example, a reflecting element can be placed in the optical axis of the lithography system, such as in place of a process wafer (a process wafer being a wafer undergoing patterning with the assistance of the lithography system) or as part of a wafer stage. The reflecting element is used to redirect an exposure dose during a periodic cleaning or maintenance cycle of the lithography system. In particular, the reflecting element can be used to direct ultraviolet light towards surfaces of an immersion medium supply device that, during imaging of process wafers, maintains a volume of immersion medium between a final optical element of the exposure tool and the wafer. The redirected radiation can kill live biological contaminants and a subsequent purge of an immersion medium system can be used to remove dead biological contaminants and/or particles left behind after the radiation cycle.

Figure 1:
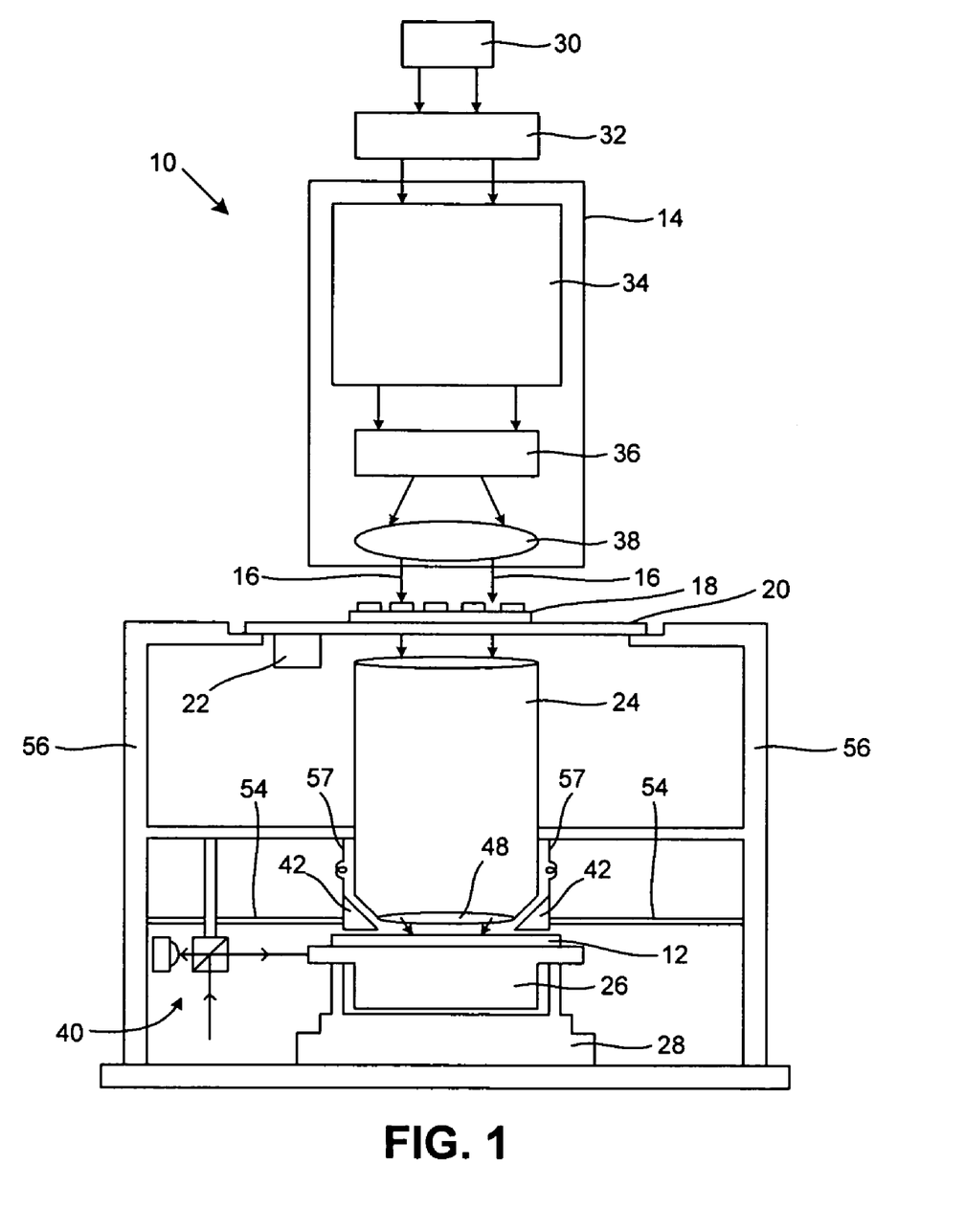
FIG. 1 is a schematic diagram of an example lithography system.

Referring to FIG. 1, schematically illustrated is an example IC processing arrangement that includes an immersion lithography system 10 used to image a pattern onto a process wafer 12, or a region thereof. The system 10 can be, for example, a step-and-repeat exposure system or a step-and-scan exposure system, but is not limited to these example systems. The system 10 can include an illumination system, or illuminator 14, that directs a projection beam in the form of electromagnetic radiation 16 toward a mask, or reticle 18. The radiation 16 can have a deep ultraviolet (DUV) wavelength, such as about 248 nm, about 193 nm or about 157 nm, although other wavelengths are possible.

The reticle 18 can be supported by a mask table 20. The mask table 20 can be connected to a positioning device 22 for positioning the reticle 18 with respect to a projection system 24. The projection system 24 directs the radiation 16, as patterned by the reticle 18, toward the wafer 12, which can be coated with a photoresist. The wafer 12 can be supported by a wafer table 26. The wafer table 26 can be connected to a positioning device 28 for positioning the wafer 12 with respect to the projection system 24. The projection system 24, which can include, for example, a refractive projection lens or lens assembly, images the pattern imparted to the projection beam 16 by the reticle 18 onto a target portion of the wafer 12. In the illustrated embodiment, the system 10 is a transmissive system using a transmissive reticle 18. However, the system 10 can alternatively be a reflective system, such as a system that uses a programmable mirror array or patterned reflector.

The illuminator 14 receives radiation from a radiation source 30, such as a laser. The source 30 and the lithographic system 10 may be separate assemblies. In such cases, the source 30 is not considered to form part of the lithographic system 10. The radiation can be passed from the source 30 to the illuminator 14 using a delivery assembly 32 having, for example, suitable directing mirrors and/or a beam expander. In other embodiments, the source 30 may be an integral part of the lithographic system 10. The source 30 and the illuminator 14, together with the beam delivery system 32, if present, may be referred to as a radiation system.

The illuminator 14 can include an adjusting device 34 for adjusting the angular intensity distribution of the radiation 16. Generally, at least the outer and/or inner radial extent of the intensity distribution in a pupil plane of the illuminator 14 (respectively referred to as sigma-outer and sigma-inner) can be adjusted. In addition, the illuminator 14 can include various other components, such as an integrator 36 and a condenser 38. The illuminator 14 provides a conditioned beam of radiation 16, sometimes referred to as a projection beam. Preferably, the projection beam has a desired uniformity and intensity distribution in its cross-section.

After becoming incident on the reticle 18, the projection beam 16 passes through the projection system 24. The projection system 24 focuses the beam onto a target portion of the substrate 12. Using the positioning device 28 and a position sensor 40 (e.g. an interferometric system), the substrate table 26 can be positioned such that different target portions of the wafer 12 are placed in the path of the beam. Similarly, the positioning device 22 and another position sensor (not shown) can be used to position the mask table 20 and mask 18 with respect to the path of the beam 16. Positioning a mask 18 may be carried out, for example, after mechanical retrieval of the mask 18 from a mask library, or during a scan. In addition, positioning of the mask 18 and/or wafer 12 can be assisted by using mask alignment marks and wafer alignment marks, respectively.

If the lithographic system is used in a step mode, the mask table 20 and the wafer table 26 are kept essentially stationary during exposure of a target portion of the wafer 12. For example, an entire pattern is imparted to the projection beam and projected onto a target portion at one time using a single static exposure. Thereafter, the wafer table 26 is shifted relative to the optical axis of the projection system 24 (e.g., in a direction(s) commonly referred to as the X and/or Y directions) so that a different target portion can be exposed.

If the lithographic system is used in a scan mode, the mask table 20 and the wafer table 26 are scanned synchronously while a pattern imparted to the projection beam is projected onto the target portion of the wafer 12 using a single dynamic exposure. The velocity and direction of the wafer table 26 relative to the mask table 20 can be determined by a (de-)magnification and image reversal characteristics of the projection system 24.

In another mode, the mask table 20 is kept essentially stationary to hold a programmable patterning device, and the wafer table 26 is moved or scanned while a pattern imparted to the projection beam is projected onto a target portion of the wafer 12. In this mode, a pulsed radiation source can be employed and the programmable patterning device can be updated after each movement of the wafer table 26 or between successive radiation pulses.

As will be apparent, combinations and/or variations of the foregoing modes of operation or entirely different modes of operation for the lithographic system 10 can be employed.

Figure 2:
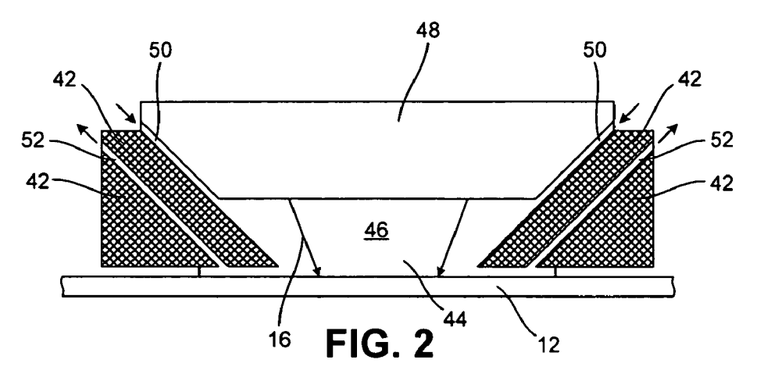
FIG. 2 is a partial cross-section an immersion medium supply device for the lithography system.

With additional reference to FIG. 2, shown is a partial cross-section of an immersion medium supply device 42 for the lithography system 10. The immersion medium supply device 42 dispenses an immersion medium 44, in the form of a liquid, such that the immersion medium 44 fills a volume 46 between a final element 48 of the projection system 24 and the wafer 12. In the illustrated embodiment, the immersion medium 44 is water, which preferably has been distilled, de-ionized and/or filtered to remove contaminants, including, for example, particulates and biological contaminants. Other liquid immersion mediums 44 are possible, including, for example, polyfluoroethers.

The supply device 42 is sometimes referred to in the art as a "seal" since the supply device 42 can be arranged with the wafer 12 to prevent or minimize leakage of the immersion medium 44 from the volume 46. Others have referred to the supply device 42 as a "shower head" since the supply device 42 can be arranged to dispense the immersion medium 44 onto the wafer 12 and to fill the volume 46. In addition, the supply device 42 can extract the immersion medium 44 from the volume 46. In some arrangements, the supply and extraction of the immersion medium 44 is carried out simultaneously. In most arrangements, the supply device 42 is an immersion medium dispensing and recovery component that is located adjacent (e.g., surrounds) a final optical element 48 of the projection system 24. The final optical element 48 can be, for example, a lens or other optical component.

The supply device 42 can take on a number of arrangements and is not limited to the illustrated embodiment. Rather, the present invention is applicable to any immersion lithography system where the presence and/or growth of biological contaminants is a concern.

In the illustrated embodiment, the supply device 42 is arranged with respect to the final element 48 of the projection system 24 and the upper surface of the wafer 12 to define the volume 46. For example, the supply device 42 can be partially disposed between the final element 48 and the wafer 12 and/or at least partially surrounding the final element 48.

With immersion medium flow generally indicated by arrows in FIG. 2, the supply device 42 can have at least one liquid inlet passage 50 and at least one liquid outlet passage 52. In the illustrated embodiment, the inlet passage 50 is defined by corresponding surfaces of the final element 48 and the dispensing device 42, but could alternatively be defined by a hollow section of the supply device 42. The outlet passage 52 is defined by a hollow section of the supply device 42. In the illustrated embodiment, the outlet passage 52 is located radially outward of the inlet passage 50 with respect to the optical axis of the projection system 24. As will be appreciated, the relative locations of the inlet passage 50 and the outlet passage 52 can be reversed, and/or additional inlet and/or outlet passages can be present. In one embodiment, a liquid seal is formed by a flow of liquid from the inlet passage 50 to the outlet passage 52. For example, the liquid seal can be formed by a hydrostatic bearing defined by the flow of liquid from the inlet passage 50 to the outlet passage 52. In embodiments where the wafer 12 moves relative to the supply device 42 or at times when the wafer 12 is moved relative to the supply device 42, the bearing may be considered a hydrodynamic bearing. In either case, the hydraulic bearing can provide mechanical support to the supply device 42 (e.g., hold the supply device 52 in spaced relationship to the wafer 12), as well as provide a liquid seal to prevent or minimize leakage of the immersion medium 44 from the volume 46.

Although not illustrated, a vacuum outlet can be formed in the supply device 42. The vacuum outlet can be located radially outward of the passages 50 and 52 with respect to the optical axis and used for extracting any liquid that may escape from the liquid seal.

FIG. 2 illustrates the supply device 42 in cross section. It will be appreciated that the inlet passage 50 and the outlet passage 52 can each extend continuously around the liquid filled volume 46 and, therefore, would each have the appearance of a groove or aperture when viewed from the upper surface of the wafer 12. These grooves can be annular, rectangular, polygonal, or an other appropriate shape. Alternatively the passages through the supply device 42 can be provided at discrete locations and mate with corresponding continuous grooves formed in the surface of the supply device 42. In other arrangements, the immersion medium input and/or output apertures do not extend continuously around the final element 48.

As best shown in FIG. 1, at least one member 54 disposed transverse to the optical axis can connect the supply device 42 to sides of a reference frame 56. The member 54 can assist in maintaining the lateral position of the supply device 52. For example, the member 54 can keep the supply device 42 relatively stationary in a plane perpendicular to the optical axis of the projection system 24 while allowing relative movement in a direction along the optical axis. Springs 57 connected between the supply device 42 and the reference frame 56 can be used to apply a biasing force to the supply device 42 and against the force developed by the hydraulic bearing.

In one embodiment, the lower surface of the supply device 42 can be positioned about 10 microns to about 500 microns above the upper surface of the wafer 12. As will be appreciated, the size of this gap can be altered by altering the pressure of the hydraulic bearing and/or by altering the bias force applied by the springs 57.

As indicated, the supply device 42 is not limited to the illustrated embodiment. Several other example embodiments for a supply device 42 are described in U.S. Patent Application Publication Nos. 2004/0207824, 2004/0257544, 2005/0007570, 2005/0018155 and 2005/0024609, the disclosures of which are herein incorporated by reference in their entireties.

Figure 3:
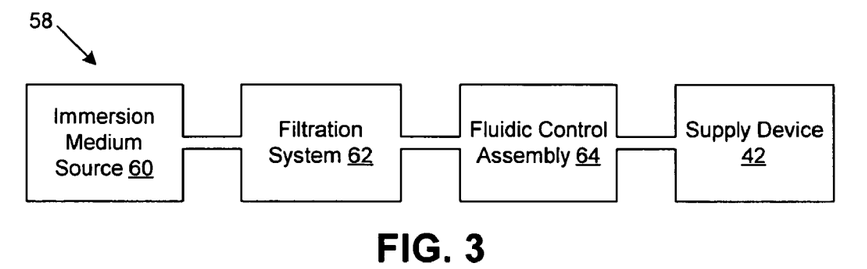
FIG. 3 is a schematic block diagram of an immersion medium system for the lithography system.

With additional reference to FIG. 3 shown is a schematic block diagram of an immersion medium system 58 for the lithography system 10. The illustrated system 58 is directed to only high-level elements of such a system 58 to orient the reader to the general operation of such as system. It will be appreciated that the actual implementation of the system 58 can vary greatly. For example, one or more of the components can be omitted, components can be added and the order of the components can be altered. Details of the construction and operation of the system 58 are omitted as these details will vary among different immersion medium handling systems.

In general, the system 58 can include an immersion medium source 60 that serves as a reservoir of the immersion medium 44. The source 60 can be fluidically connected to a filtration system 62 used to cleanse the immersion medium 44 and/or remove contaminants therefrom. The filtration system 62 can be configured to remove biological contamination from the immersion medium 44, including bacteria, algae, mold and so forth. Following filtration, the immersion medium 44 can be retained in an intermediate reservoir (not shown) and passed to the supply device 42 for filling the volume 46 and creating the above-mentioned hydraulic bearing under the control and regulation of a fluidic control assembly 64.

Even though the immersion medium 44 should be highly purified and substantially free of contaminants, including biological contaminants, when exiting the filtration system 62 and the lithography system 10 is usually operated in a highly controlled environment (e.g., a clean room), the applicants have become aware of the presence of biological contaminants in the immersion medium 44 and/or growing on surfaces of the supply device 42. The source of these contaminants vary and may result from human interaction with the lithography system 10, the mask 18 and/or the wafer 12. Biological matter present on anything brought near or into contact with the lithographic system 10, the mask 18 and/or the wafer 12 may serve as a source for contamination of the immersion medium 44 and/or the supply device 42.

The liquid environment of the immersion lithograph system 10, especially when the immersion medium 44 is water, can support life and the growth of biological contaminants. As indicated, these contaminants can cause defects on process wafers 12 during patterning. In some situations, it may be desirable to include relatively stagnant regions of immersion medium 44 within the supply device 42 to achieve desired fluid dynamics for use in the immersion lithography process. The presence of biological contamination can be exacerbated by the presence these stagnant regions.

Figures 4, 5:
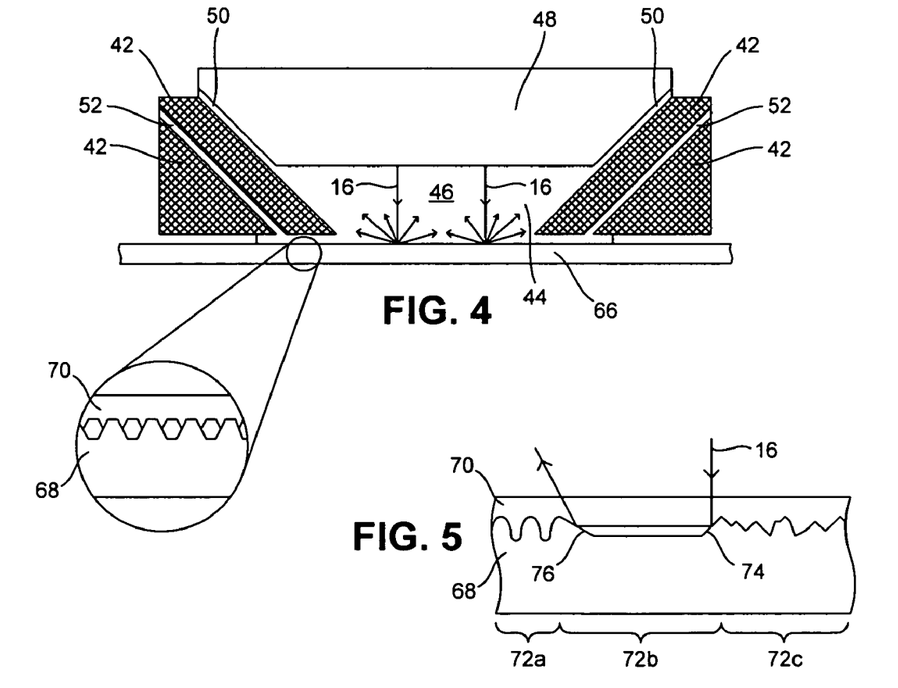
FIG. 4 is a partial cross-section of the immersion medium supply device during a maintenance cycle for reducing biological contamination using a reflecting element.
FIG. 5 is a partial cross-section of the reflecting element having various example reflective surface embodiments.

Turning now to FIG. 4, shown is a partial cross-section of the immersion medium supply device 42 during a maintenance cycle of the lithography system 10 for reducing biological contamination using a reflecting element 66. As illustrated, the maintenance cycle can be carried out in the presence of the immersion medium 44. For example, the system 58 can be operated to fill the volume 46 between the final optical element 48 and the reflecting element 66 and to create the hydraulic bearing. Alternatively, or in addition to carrying out the maintenance cycle in the presence of the immersion medium, the maintenance cycle can be carried out in the absence of the immersion medium 44. For example, prior to exposing the reflecting element 66, the immersion medium can be purged from the volume 46 and/or supply device 42 to the greatest extent possible with the fluidic control assembly 64.

The maintenance cycle involves placing the reflecting element 66 in the optical axis of the projection system 24 to redirect (e.g., reflect) radiation 16 output by the final optical element 48 toward the volume 46 and/or portions of the supply device 42. In one embodiment, the reflecting element 66 has properties of a diffuse mirror to reflect incident radiation 16 at many angles, such as by scattering incident radiation to expose as much of the supply device 42 as possible, including at least some of the interior surfaces of the supply device 42 (e.g., walls of the passages 50, 52). In another embodiment, the reflecting element 66 can include a particular geometrical design to direct radiation toward specific areas of the supply device 42 and/or the volume 46.

Preferably, the radiation 16 is the same radiation 16 normally used to expose process wafers 12. For example, the radiation 16 can originate from the illumination source 30, pass through the illuminator 14, pass through the projection system 24, exit the final element 48 and traverse the volume 46 prior to becoming incident on the reflecting element 66. The illumination source 30, the illuminator and/or the projection system 24 can be selected and/or optimized to produce a radiation pattern incident on the reflecting element 66 to attain a desired reflection pattern. For example, the exposure wavelength can be selected by changing the illumination source 30. In some situations, however, changing the illumination source 30 may be impractical if lithography system is arranged for using a particular wavelength of radiation 16. As another example, the illuminator 14 characteristics can be changed, such as by configuring the illuminator 14 to produce circular illumination, dipole illumination, quadrapole illumination and so forth. A mask, or reticle, can be used for the maintenance cycle exposure to impart the radiation with a pattern, or a reticle can be omitted to pass the radiation 16 directly from the illuminator 14 to the projection system 24.

In one embodiment, the supply device 42 can be made from a material that is not generally transmissive of the exposure wavelength, such as aluminum or stainless steel. In another embodiment, the supply device 42 can be made from a material that is transmissive of the exposure wavelength (such as silicon oxide, quartz or fused silica) to allow reflected radiation to come into contact with surfaces located optically "behind" surfaces that would otherwise stop the perpetuation of the radiation.

As indicated, the reflecting element 66 can include a reflective surface (e.g., a diffuse mirror surface) for reflecting the radiation 16 output by the final element 48 of the projection system in a number of directions (e.g., scattered throughout the volume 46). The reflected radiation can become incident on the supply device 42 and illuminate (or "fill") all or substantially all of the volume 46. Living biological contaminants on surfaces exposed to the reflected radiation will tend to die as biological contaminants do not have a significantly high survival rate when subjected to the dose of ultraviolet radiation that can be generated by the lithography system 10. Also, in embodiments where the maintenance cycle is carried out in the presence of the immersion medium 44 (e.g., immersion medium 44 is used to fill the volume 46 and create the hydraulic bearing and/or is cycled through the volume 46), the reflected radiation can kill biological contaminants borne by the immersion medium 44.

In one embodiment, the maintenance cycle to kill biological contamination can include positioning the reflecting element 66 in the optical axis of the projection system 24 and exposing the reflecting element 66 to radiation 16 so that radiation 16 incident on the reflecting element 66 is reflected into the volume 46 and/or onto surfaces of the supply device 42. Conducting at least these steps between the exposure of process wafers 12 can inhibit biological contamination growth without adversely affecting throughput of wafers. As will be appreciated, such steps need not be carried out between exposing every successive pair of process wafers 12, but can be performed periodically.

The exposure during the maintenance cycle can be of sufficient duration, intensity and reflection pattern to kill at least a substantial percentage (e.g., greater than 90%) of biological contaminants in the volume 46, on the surface of the final optical element 48 and/or on illuminated surfaces of the supply device 42. It is noted that although the same wavelength radiation is present during exposure of process wafers 12 in conventional immersion lithography (e.g., "normal" operation of the lithography system 10 does not include use of the reflecting element 66), instances of biological contamination growth have indicated that additional maintenance is desirable. That is, even with the use of the filtration system 62 (FIG. 3) and the use of ultraviolet exposure doses to image process wafers 12, the immersion lithographic system 10 is at risk for biological contamination.

Following exposure to the radiation, the system can be purged with the immersion medium 44 used to immerse the process wafers 12 in the lithography system 10. The purge can remove all or at least some of any remaining biological contaminants, which will typically take the form of dead biological contaminants. As will be appreciated, the system need not be purged after each exposure to kill biological contamination. For instance, purging can be conducted in every few exposures and/or in conjunction with a purge conducted as part of an existing maintenance routine.

The reflecting element 66 can be embodied in a number of ways. For example, the reflecting element 66 can be incorporated into a part of the wafer stage 26 or can take the form of a separate piece of equipment that is placed on or temporarily replaces the wafer stage 26. In the illustrated embodiment, the reflecting element 66 is a specially fabricated wafer that is loaded onto the wafer stage 26 in the manner that one would load the process wafer 12 onto the wafer stage 26. The reflecting element 66 can continuously or non-continuously underlie the volume 46 and/or the supply device 42. For example, the reflecting element 66 may be disc-shaped, annular or have any other appropriate shape or geometry.

The reflecting element 66 can be made using a variety of techniques and out of a variety of materials that are compatible with the lithography system 10. For example, materials used in construction of a reflection layer 68 that performs the reflecting function can include any metal or metal oxide that provides reflectivity at the exposure wavelength. The reflecting surface of the reflection layer 68 can be formed to function as a diffuse mirror. The reflecting surface can be machined (e.g., micromachined or nanomachined), etched, chemically treated, subjected to abrasion or the like to form a random or non-random pattern that provides a desired random or non-random reflectivity pattern. In this manner, incident radiation can be reflected at predetermined angles, at random angles or a combination of predetermined and random angles.

In the embodiment of FIG. 4, the reflection layer 68 has a patterned upper surface. In the illustrated embodiment, the pattern comprises offset rows of truncated pyramidal structures (e.g., each structure having generally sloped walls and a generally flat top). Of course, the structures need not be truncated and/or can be formed as a regular array (e.g., rows of the structures are not offset from adjacent rows).

It may be desirable to encapsulate the reflection layer 68 to protect the layer 68, minimize contamination from the reflection layer 68 into the immersion medium 44 (e.g., minimize the release of metal from the reflection layer 68 into the immersion medium and/or minimize chemical interaction of the immersion medium 44 and the reflection layer 68) and/or provide a relatively smooth upper surface for the overall reflecting element 66. For example, an encapsulation layer 70 can be formed over the layer 68. The encapsulation layer 70 can be at least partially transmissive of the exposure wavelength. The encapsulation layer 70 can be made from, for example, a dielectric film. Suitable dielectric films can include silicon oxide and silicon nitride. Alternatively, the reflection layer 68 need not be encapsulated by an overlying layer or may be partially encapsulated. Also, the reflection layer 68 can be formed on an underlying substrate (not shown) that is made from any suitable material.

Alternative patterns for the upper surface of the reflection layer 68 include angular grooves, concentric grooves that have any appropriate geometric shape including circles, ovals, squares, polygons, etc., arrays of pointed or truncated cones having a smaller end directed towards the final element 48, and so forth. Of course, the pattern is not limited to any of the patterns shown or described herein. The surfaces of pattern structures can be curved or rounded over and/or the surfaces of the pattern structures can be linear.

FIG. 5 illustrates several additional example surfaces for the reflection layer 68. The reflection layer 68 can include plural types of surface patterns, as illustrated, or can have a single type of surface pattern. A first region 72a of the reflection layer 68 in FIG. 5 has a grooved pattern where the surfaces of the grooves are curved. A second region 72b of the reflection layer 68 is formed to guide incident radiation 16 across the reflecting element 66 by a first reflective structure 74 and redirect radiation towards a particular location using a second reflective structure 76. A third region 72c of the reflection layer 68 has a random texture defined by a plurality of linear surface segments arranged at various angles with respect to the optical axis of the projection system 24.

In the description thus far, the source 30 and the illuminator 14 has been used to generate the radiation 16 introduced to reduce biological contamination. As will be appreciated, other sources of the radiation 16 are possible.

Figure 6:
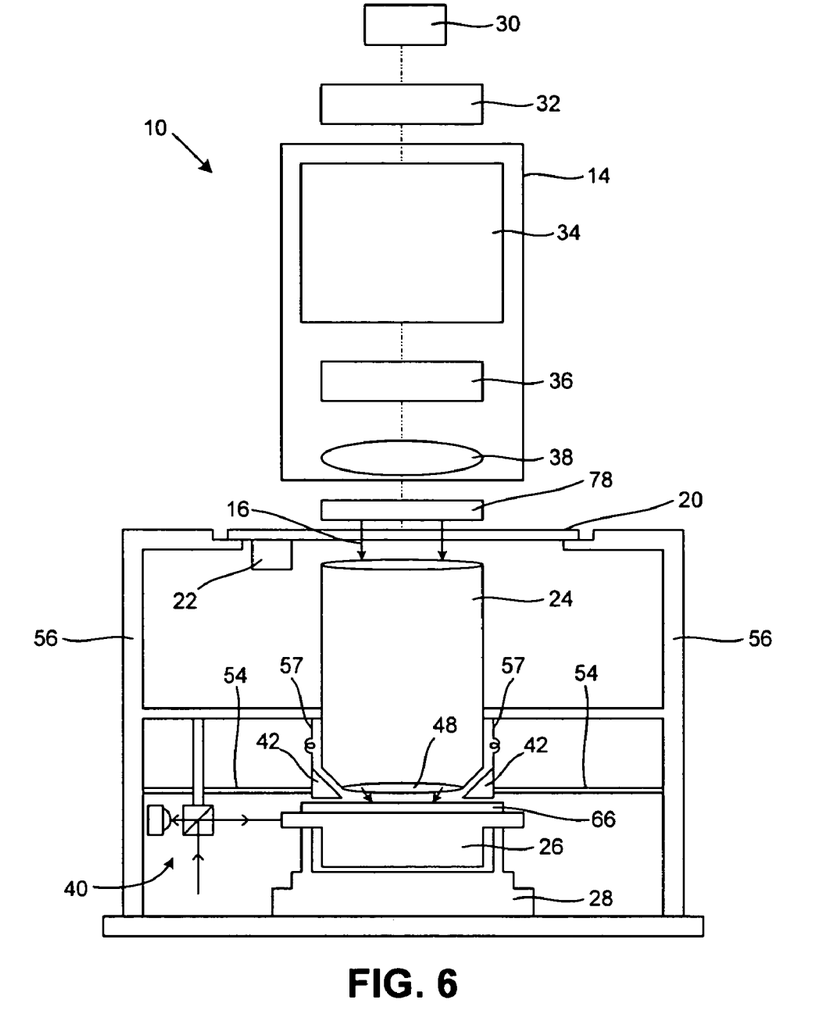
FIG. 6 is a schematic diagram of the lithography system in an alternative arrangement for reducing biological contamination.

With additional reference to FIG. 6, shown is the lithography system 10 in an alternative arrangement for reducing biological contamination. In particular, a secondary radiation source 78 is used to generate the radiation 16. In the illustrated embodiment, the radiation source 78, or an output portion thereof, is placed between the illuminator 14 and the projection system 24. However, other locations are possible, such as optically prior to the illuminator 14 and in place of the source 30. In another embodiment, the radiation source 78, or an output portion thereof, can be placed in the volume between the final element 48 and the reflecting element 66.

The radiation source 78 can be any suitable source of radiation 16. For example, the radiation source 78 can include a compact ultraviolet (UV) laser, a broadband UV bulb or other device. In one embodiment, the radiation source 78 can generate radiation at a wavelength (or wavelengths) that is (are) optimized to kill biological contaminants. In some cases, the radiation source 78 can include reflecting elements, lenses, optical elements, waveguides (e.g., fiber optics) and/or other components to condition, transport, direct and/or transmit output radiation 16 to a desired location(s) relative to the lithography system 10.

The radiation 16 output by the radiation 78 can be directed to become incident on the reflecting element 66. For example, the radiation 16 can be directed through the projection system 24, as illustrated, or projected directly onto the reflecting element 66. In turn, the reflecting element 66 redirects the radiation 16 in the manner described above when the source 30 functions to generate the radiation 16 to kill biological contaminants with respect to at least one the volume 46 or the supply device 42.

Figure 7:
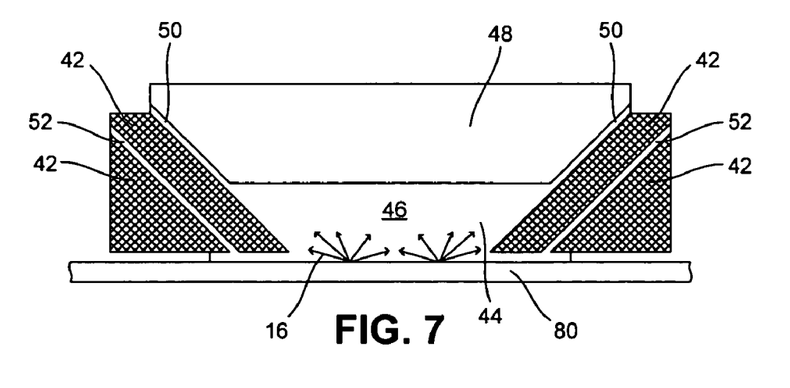
FIG. 7 is a partial cross-section of the immersion medium supply device during a maintenance cycle for reducing biological contamination using an irradiating element.

FIG. 7 illustrates another embodiment of an arrangement for the lithography system 10 used for reducing biological contamination. In the embodiment of FIG. 7, an irradiating element 80 replaces the reflecting element 66. However, it will be appreciated that the irradiating element 80 can be used in conjunction with the reflecting element 66 and/or other optical devices. Also, the irradiating element 80 can include any appropriate optical or reflecting component and, therefore, can include the reflecting element 66. Furthermore, the irradiating element 80 can include any appropriate radiation source and, therefore, can include the secondary radiation source 78. The irradiating element 80 is configured to direct radiation 16 into the volume 46 and/or towards the supply device 42.

The irradiating element 80 can be embodied in a number of ways. For example, the irradiating element 80 can be incorporated into a part of the wafer stage 26 or can take the form of a separate piece of equipment that is placed on or temporarily replaces the wafer stage 26. In the illustrated embodiment, the irradiating element 80 is a specially fabricated device that is loaded onto the wafer stage 26 in the manner that one would load the process wafer 12 onto the wafer stage 26. The irradiating element 80 can continuously or non-continuously underlie the volume 46 and/or the supply device 42. For example, the irradiating element 80 may be disc-shaped, annular or have any other appropriate shape or geometry.

One example irradiating element 80 can include a series of micro lenses, each of which can direct radiation 16 in a plurality of directions. The radiation 16 can originate from inside the irradiating element 80 or can be carried to irradiating element 80 for transmission through a surface (or surfaces) thereof. In one arrangement, a bundle of fiber optic waveguides can transport radiation 16 from an external source to an inside of the irradiating element 80, from which the radiation 16 is then directed outward into the volume 46 and/or towards the supply device 42. Each fiber optic waveguide can be associated with a corresponding output element, such as a lens.

Although immersion lithography has advantages over conventional, dry lithography, the use of an immersion medium 44 can lead to complications not present in dry lithography systems. For instance, the immersion medium can promote the growth of biological contamination, such as bacteria. Bacteria growth can be most prevalent when the immersion medium is water, but other immersion mediums may also sustain the presence of biological contamination. Disclosed herein is a method of reducing biological contamination in an immersion lithography system and structural components useful to reduce biological contamination in an immersion lithography system. Radiation, in the form of ultraviolet light, from the lithography system (sometimes referred to as an exposure tool) or another source is used to kill the biological contamination.

The method and apparatus described herein have the advantages of not introducing chemicals into the lithographic system and avoiding a loss in wafer processing throughput by using a more time consuming cleaning technique. In one embodiment, the maintenance cycle to kill biological contaminants and/or purge dead biological contaminants can be carried out in conjunction with regular cleaning and maintenance of the lithography system, which may include a purge of the immersion medium. Killing biological contamination, and in particular bacteria, on a regular basis (e.g., at regular time-based and/or use-based intervals) can assist in suppressing growth of colonies of the biological matter. As a result, the lithographic system can be kept clean and can have a lower occurrence of defects caused by the presence of biological contamination.

Although particular embodiments of the invention have been described in detail, it is understood that the invention is not limited correspondingly in scope, but includes all changes, modifications and equivalents coming within the spirit and terms of the claims appended hereto.

What is claimed is:

1. A method of reducing biological contamination in an immersion lithography system, comprising:
   placing a reflecting element with respect to an optical axis of a projection system of the lithographic system and optically downstream from a final element of the projection system; and
   exposing the reflecting element with an exposure dose, the reflecting element redirecting radiation from the exposure dose to kill biological contaminates present with respect to at least one of i) a volume between the final element of the projection system and the reflecting element or ii) an immersion medium supply device disposed adjacent the volume.

2. The method according to claim 1, wherein the radiation of the exposure dose is at least one of ultraviolet radiation originating from an illumination source used by the lithographic system to generate radiation for imaging a process wafer or a secondary radiation source.

3. The method according to claim 1, wherein exposing the reflecting element is carried out in at least one of the presence of an immersion medium filling the volume or the absence of an immersion medium filling the volume.

4. The method according to claim 1, further comprising purging the lithographic system to remove dead biological contaminants with an immersion medium used to immerse a process wafer associated with the lithographic system.

5. The method according to claim 1, wherein the reflecting element includes a diffuse mirror surface.

6. The method according to claim 1, wherein the reflecting element is a wafer that takes the place of a process wafer during the exposing.

7. The method according to claim 1, wherein the reflecting element is formed as part of a wafer table used to support and position process wafers in the lithographic system.

8. The method according to claim 1, wherein the reflecting element includes a layer having a reflecting surface and an encapsulation layer overlying the reflecting surface.

9. The method according to claim 1, wherein the exposing is carried out between imaging of a first selected pair of process wafers and repeated between imaging of a second selected pair of process wafers.

10. A method of reducing biological contamination in an immersion lithography system, comprising:
    placing an irradiating element with respect to an optical axis of a projection system of the lithographic system and optically downstream from a final element of the projection system;
    transporting radiation from a radiation source located outside the irradiating element into the irradiating element; and
    directing the radiation from the irradiating element to kill biological contaminates present with respect to at least one of i) a volume adjacent to the final element of the projection system or ii) an immersion medium supply device disposed adjacent the final element.

11. An immersion lithography system configured to reduce biological contamination, comprising:
a projection system having a final element;
an immersion medium supply device adjacent the final element; and
a reflecting element placed with respect to an optical axis of the projection system and optically downstream from the final element of the projection system such that a volume is formed between the final element and the reflecting element, and when the reflecting element is exposed with an exposure dose the reflecting element redirects radiation from the exposure dose to kill biological contaminants present with respect to at least one of the volume or the immersion medium supply device.

12. The system according to claim 11, wherein the radiation of the exposure dose is at least one of ultraviolet radiation originating from an illumination source used by the lithographic system to generate radiation for imaging a process wafer or a secondary radiation source.

13. The system according to claim 11, further comprising an immersion medium filling the volume during the exposure dose.

14. The system according to claim 11, wherein the reflecting element includes a diffuse mirror surface.

15. The system according to claim 11, wherein the reflecting element includes a layer having a reflecting surface having at least one of a random pattern or a non-random pattern.

16. The system according to claim 11, wherein the reflecting element is a wafer that takes the place of a process wafer.

17. The system according to claim 11, wherein the reflecting element is formed as part of a wafer table used to support and position process wafers in the lithographic system.

18. The system according to claim 11, wherein the reflecting element includes a layer having a reflecting surface and an encapsulation layer overlying the reflecting surface.

19. The system according to claim 18, wherein the layer having the reflecting surface is made from a metal or metal oxide and the encapsulation layer is made from a dielectric film.

20. An immersion lithography system configured to reduce biological contamination, comprising:
a projection system having a final element;
an immersion medium supply device adjacent the final element;
an irradiating element placed with respect to an optical axis of the projection system and optically downstream from the final element of the projection system; and
a radiation source external to the irradiating element and optically coupled to the irradiating element so that radiation is transported into the irradiating element and directed out of the irradiating element so as to direct radiation to kill biological contaminants present with respect to at least one of a volume adjacent the final element or the immersion medium supply device.

* * * * *